(12) United States Patent
Ishiyama et al.

(10) Patent No.: US 8,148,567 B2
(45) Date of Patent: Apr. 3, 2012

(54) PROCESS FOR PRODUCING URETHANE (METH)ACRYLATE

(75) Inventors: Fumihiko Ishiyama, Sakura (JP); Takeshi Hizawa, Sakura (JP); Hideki Watanabe, Ichihara (JP)

(73) Assignee: DIC Corporation, Tokyo (JP)

( * ) Notice: Subject to any disclaimer, the term of this patent is extended or adjusted under 35 U.S.C. 154(b) by 0 days.

(21) Appl. No.: 12/922,207

(22) PCT Filed: Mar. 12, 2009

(86) PCT No.: PCT/JP2009/054732
§ 371 (c)(1),
(2), (4) Date: Sep. 13, 2010

(87) PCT Pub. No.: WO2009/113608
PCT Pub. Date: Sep. 17, 2009

(65) Prior Publication Data
US 2011/0087041 A1 Apr. 14, 2011

(30) Foreign Application Priority Data
Mar. 14, 2008 (JP) ................................. 2008-065709

(51) Int. Cl.
*C07C 269/00* (2006.01)
(52) U.S. Cl. .............. 560/26; 560/25; 560/27; 560/115; 560/220; 560/221
(58) Field of Classification Search ........................ None
See application file for complete search history.

(56) References Cited

U.S. PATENT DOCUMENTS

| 4,920,190 A * | 4/1990 | Lina et al. ...................... 526/288 |
| 5,008,436 A * | 4/1991 | Muller et al. .................... 560/26 |

FOREIGN PATENT DOCUMENTS

| JP | 62-132850 A | 6/1987 |
| JP | 03-020255 A | 1/1991 |
| JP | 08-109230 A | 4/1996 |
| JP | 2001-340753 A | 12/2001 |
| JP | 2003-535166 A | 11/2003 |
| JP | 2005-002004 A | 1/2005 |
| JP | 2006-111574 A | 4/2006 |

OTHER PUBLICATIONS

International Search Report dated Jun. 9, 2009, issued for PCT/JP2009/054732.

* cited by examiner

*Primary Examiner* — Sudhakar Katakam
(74) *Attorney, Agent, or Firm* — Edwards Wildman Palmer LLP; James E. Armstrong, IV; Junko Harada (57) ABSTRACT

An object of the present invention is to provide a process for producing a urethane (meth)acrylate safely with good productivity, and for achieving the object, the invention provides a process for continuously producing a urethane (meth)acrylate, containing causing a mixed liquid of a compound (A) having a hydroxyl group and a (meth)acryloyl group and a compound (B) having an isocyanate group to pass continuously and densely through a tubular microchannel formed in a heat-conducting reaction device, and reacting the hydroxyl group of the compound (A) with the isocyanate group of the compound (B), in which the tubular microchannel in the reaction device has a space size making a fluid cross-sectional area, through which the mixed liquid passes densely, of from 0.1 to 4.0 mm$^2$, and the process contains heating the heat-conducting reaction device to a temperature of from 100 to 250° C., reacting the mixed liquid to provide a Reynolds number of a reaction liquid passing through the tubular microchannel in a range of from 0.2 to 300, and after completing reaction, cooling continuously a reaction product discharged from the heat-conducting reaction device.

12 Claims, 3 Drawing Sheets

PROCESS FOR PRODUCING URETHANE (METH)ACRYLATE

TECHNICAL FIELD

The present invention relates to a production process capable of producing a urethane (meth)acrylate safely and continuously with good productivity.

BACKGROUND ART

A urethane (meth)acrylate has hitherto been produced by a batch process using a reaction vessel. In general, a urethane (meth)acrylate is produced by reacting a hydroxyl group of a compound having a hydroxyl group and a (meth) acryloyl group with an isocyanate group of a compound having an isocyanate group. The reaction between a hydroxyl group and an isocyanate group is exothermic reaction. In the process of the exothermic reaction proceeding, when the temperature of the reaction system is abnormally increased due to accumulation of the reaction heat, the (meth)acryloyl groups are bonded to each other to cause runaway reaction where the reaction product is gelled. Accordingly, for suppressing excessive generation and accumulation of the reaction heat, which bring about runaway reaction, precise temperature control and efficient removal of heat are demanded, but in the case of a large reaction system, such as an industrial production scale, it is difficult to achieve them due to efficiency of agitation, heat removal capability and the like.

The runaway reaction occurring brings about gasification of the unreacted raw materials due to heat generation on the runaway reaction, and gasification due to decomposition of the urethane (meth)acrylate produced. The phenomena may result in quick increase of the pressure inside the reaction system to cause fatal breakage of the equipment in some cases. For preventing the equipment from being broken, a measure of opening the pressure accumulated in the system and a measure of discharging the contents to the outside of the system are taken by opening a manhole, a safety valve, a rupture disk, an explosion vent or the like provided on the reaction vessel. However, the measures require large-scaled equipments, which bring about an increased investment cost and a large occupied area, and thus only poor productivity is obtained.

A method of adding a polymerization inhibitor is known as a measure for terminating runaway reaction occurring during production of a urethane (meth)acrylate. It is necessary in the method that a polymerization inhibitor is dispersed and dissolved in the reaction system in a very short period of time.

However, the reaction system is liable to be increased in viscosity upon gelling, which bring about such a problem that it is considerably difficult to disperse and dissolve a polymerization inhibitor in the reaction system in a very short period of time. In addition, the driving capacity of the agitation blade for agitating the reaction system becomes insufficient against the quick increase of the viscosity due to the runaway reaction, which results in not only the failure of sufficient dispersion and dissolution of the polymerization inhibitor in the reaction system, but also such a problem that the equipment suffer fatal breakage, such as malfunction of the agitating device due to application of load. The problem becomes serious in the case where a diluent solvent or the like is not used upon producing a urethane (meth)acrylate.

As a measure for facilitating dispersion and dissolution of a polymerization inhibitor in a reaction system, such a method may be used that a polymerization inhibitor is used after dissolving in a solvent or the like, but for addressing occurrence of runaway reaction, it is necessary to prepare in advance a large amount of a solution containing a polymerization inhibitor dissolved in a solvent. Accordingly, the cost of production of a urethane (meth)acrylate is increased. A polymerization inhibitor contains a mutagenic substance and thus is necessarily handled with adequate care.

As a measure for suppressing runaway reaction from occurring upon production of a urethane (meth)acrylate, such a method has been known that a solvent is made present in the reaction system, thereby decreasing the concentration of the polymerizable compound in the system and simultaneously decreasing the viscosity of the fluid, which is increased associated with the progress of the reaction, for enhancing the controllability of the reaction. In the method, however, the solvent is necessarily recovered after completing the reaction, and the yield ratio per reaction vessel is decreased due to the use of the solvent, which impair the productivity. Furthermore, the resin composition thus obtained may have a problem in quality due to the solvent remaining in a slight amount therein.

The production of a urethane (meth)acrylate may not have good productivity due to the aforementioned measures for addressing runaway reaction. Furthermore, even with the measures for addressing runaway reaction performed, it is the current situation that a urethane (meth)acrylate is produced with poor efficiency under conditions that do not cause runaway reaction, for example, at a low temperature of 100° C. or less, preferably 80° C. or less, for a prolonged period of time of from 5 to 7 hours (see, for example, Patent Document 1).

As a production method capable of preventing heating with the reaction heat, suppressing side reaction, such as multimerization, and providing a high reaction rate, such a method for producing a ring-opening reaction product of an epoxy compound is proposed that an epoxy compound and a compound having a hydroxyl group are caused to pass through a channel having a fluid cross-sectional area of from 300 to 1,000,000 $\mu m^2$ (from $3 \times 10^4$ to 1 $mm^2$), and the compounds are made in contact with each other to perform ring-opening addition reaction (see, for example, Patent Document 2). However, the production method disclosed in Patent Document 2 is limited to the ring-opening reaction of an epoxy compound, and fails to disclose any measure for preventing runaway reaction in polymerization of a (meth)acryloyl group, which is an issue in the production of a urethane (meth)acrylate Furthermore, a long period of 160 minutes is required for reacting the epoxy compound and the compound having a hydroxyl group sufficiently (for example, to a reaction rate of 98%) in the channel, and thus the production efficiency is considerably poor.

Patent Document 1: JP-A-08-109230
Patent Document 2: JP-A-2006-111574

DISCLOSURE OF THE INVENTION

Problems to be Solved by the Invention

An object of the present invention is to provide a process for producing a urethane (meth)acrylate safely with good productivity.

Means for Solving the Problems

As a result of earnest investigations made by the inventors, it has been found that by using a heat-conducting reaction device having a tubular microchannel formed therein, upon causing a mixed liquid of a compound (A) having a hydroxyl group and a (meth)acryloyl group and a compound (B) having an isocyanate group to pass continuously and densely through the tubular microchannel, and reacting the hydroxyl group of the compound (A) with the isocyanate group of the compound (B), the reaction device having a tubular microchannel has a space size making a fluid cross-sectional area, through which the mixed liquid passes densely, of from 0.1 to 4.0 mm$^2$, and the reaction liquid is caused to pass through the tubular microchannel to provide a Reynolds number in a range of from 0.2 to 300, whereby mixture by molecular diffusion proceeds associated with a microturbulent flow in the microchannel, the flow in which has been ordinarily considered to be a laminar flow, and thus the compound (A) and the compound (B) are actively in contact with each other, it has also been found that by heating the heat-conducting reaction device to a temperature of from 100 to 250° C., which cannot be employed in an ordinary batch system, the reaction efficiency between the hydroxyl group and the isocyanate group is enhanced, and the capacity of a urethane (meth)acrylate discharged from the tubular microchannel after completing the urethanation reaction is smaller than that in the batch system and thus can be easily controlled in temperature by continuously cooling, whereby consequently runaway reaction of (meth)acryloyl groups is hard to occur, and a urethane (meth)acrylate can be produced with good productivity since the urethanation reaction occurs in a short period of time. Thus, the invention has been completed.

The invention provides a process for continuously producing a urethane (meth)acrylate, containing causing a mixed liquid of a compound (A) having a hydroxyl group and a (meth)acryloyl group and a compound (B) having an isocyanate group to pass continuously and densely through a tubular microchannel formed in a heat-conducting reaction device, and reacting the hydroxyl group of the compound (A) with the isocyanate group of the compound (B), the tubular microchannel in the reaction device having a space size making a fluid cross-sectional area, through which the mixed liquid passes densely, of from 0.1 to 4.0 mm$^2$, and the process containing heating the heat-conducting reaction device to a temperature of from 100 to 250° C., reacting the mixed liquid to provide a Reynolds number of a reaction liquid passing through the tubular microchannel in a range of from 0.2 to 300, and after completing reaction, cooling continuously a reaction product discharged from the heat-conducting reaction device.

Advantages of the Invention

According to the production process of the invention, such a production process can be provided that is capable of producing a urethane (meth)acrylate safely with good productivity. Furthermore, the process is dispense with large-scaled equipments, and reduction of investment cost and production cost is expected.

BEST MODE FOR CARRYING OUT THE INVENTION

The compound (A) used in the invention has a hydroxyl group and a (meth)acryloyl group. The compound (A) is not particularly limited and may be a solid or a liquid having a high viscosity at ordinary temperature as far as it can be fed by such a measure as melting under heat, dissolving or dispersing without clogging the channel, and known compounds may be used therefor.

Examples of the compound (A) used in the invention include a hydroxyl group-containing (meth)acrylate compound having one (meth)acryloyl group, such as 2-hydroxyethyl (meth)acrylate, 2-hydroxypropyl (meth)acrylate, 2 hydroxybutyl (meth)acrylate, 4-hyrdoxybutyl (meth)acrylate, 2-hydroxyethylacryloyl phosphate, 2-(meth)acryloyloxyethyl-2 hydroxypropyl phthalate, caprolactone-modified 2-hyroxyethyl (meth)acrylate, and a hydroxyl group-containing (meth)acrylate compound having two or more (meth)acryloyl groups, such as 2 hydroxy-3 (meth)acryloyloxypropyl (meth)acrylate, pentaerythritol tri(meth)acrylate, dipentaerythritol penta(meth)acrylate, caprolactone-modified dipentaerythritol penta(meth)acrylate, and ethylene oxide-modified pentaerythritol tri (meth)acrylate. These compounds may be used solely or in combination of two or more of them.

In the production process of the invention, a compound having hydroxyl value of from 50 to 500 providing a large heat quantity on urethanation reaction is preferred as the compound (A) since the advantage of the invention, i.e., safe production, can be sufficiently exhibited. In particular, a compound having a high acryloyl group concentration, such as 2 hydroxyethyl (meth)acrylate, 2 hydroxypropyl (meth)acrylate or pentaerythritol triacrylate, is preferred as the compound (A) since the compound facilitates polymerization and provides a large heat quantity upon reaction, thereby attaining sufficiently the advantage of the production process of the invention.

The compound (B) used in the invention has an isocyanate group. The compound (B) is not particularly limited and may be a solid or a liquid having a high viscosity at ordinary temperature as far as it can be fed by such a measure as melting under heat, dissolving or dispersing without clogging the channel, and known compounds may be used therefor.

Examples of the compound (B) used in the invention include an isocyanate compound, such as an aromatic isocyanate compound, an aliphatic isocyanate compound and an alicyclic isocyanate compound. Specific examples thereof include tolylene diisocyanate, diphenylmethane diisocyanate, hydrogenated diphenylmethane diisocyanate, phenylmethane polyisocyanate, modified diphenylmethane diisocyanate, xylylene diisocyanate, hydrogenated xylylene diisocyanate, hexamethylene diisocyanate, trimethylhexamethylene diisocyanate, tetramethylxylylene diisocyanate, isophorone diisocyanate, norbornene diisocyanate, phenylene diisocyanate, lysine diisocyanate, lysine triisocyanate, naphthalene diisocyanate, 2-(meth)acryloyloxyethyl isocyanate, 1,1-bis(acryloylmethyl)ethyl isocyanate, phenyl isocyanate, p-toluenesulfonyl isocyanate, octadecyl isocyanate, butyl isocyanate, a trimer compound or a multimeric compound of these isocyanate compounds, an adduct type isocyanate compound, a biuret type isocyanate compound, an allophanate type isocyanate compound, a uretodione type isocyanate compound, a blocked compound of these compounds, and a reaction product of these isocyanate compounds with a polyol. These compounds may be used solely or in combination of two or more of them.

In the production process of the invention, a compound having an isocyanate percentage of from 15 to 60 providing a large heat quantity on urethanation reaction is preferred as the compound (B) since the advantage of the invention, i.e., safe production, can be sufficiently exhibited. In particular, tolylenediisocyanate (TDI), hexamethylene diisocyanate (HDI), isophorone diisocyanate (IPDI) and the like are preferred as the compound (B) since the compounds facilitate polymerization and provide a large heat quantity upon reaction, thereby attaining sufficiently the advantage of the production process of the invention.

The heat-conducting reaction device used in the process for producing a urethane (meth)acrylate of the invention has a tubular microchannel formed therein. The mixed liquid of the compound (A) having a hydroxyl group and a (meth)acryloyl group and the compound (B) having an isocyanate group is caused to pass continuously and densely through the tubular microchannel, and the hydroxyl group of the compound (A) is reacted with the isocyanate group of the compound (B), thereby producing continuously a urethane (meth)acrylate. The heat-conductive reaction device used has the tubular microchannel that has a space size making a fluid cross-sectional area, through which a liquid passes densely, of from 0.1 to 4.0 mm$^2$, thereby providing advantages of the invention, for example, the pressure loss does not become too large, good productivity is obtained, clogging of the channel is hard to occur, heating and cooling of the channel can be quickly controlled. The heat-conductive reaction device preferably has the tubular microchannel that has a space size making a fluid cross-sectional area, through which a liquid passes densely, of from 0.3 to 1.0 mm$^2$. The term "cross section" referred in the invention means the cross section in the direction perpendicular to the flow direction in the reaction channel, and the term "cross-sectional area" means an area of the cross section.

In the process for producing a urethane (meth)acrylate of the invention, it is necessary to react the mixed liquid to provide a Reynolds number of a reaction liquid passing through the tubular microchannel in a range of from 0.2 to 300. In general, when a liquid is caused to pass through a tubular microchannel having a space size making a fluid cross-sectional area, through which a liquid passes densely, of from 0.1 to 4.0 mm$^2$, the flowing liquid exhibits a laminar flow. Accordingly, in the case where the mixed liquid of the compound (A) having a hydroxyl group and a (meth)acryloyl group and the compound (B) having an isocyanate group is caused to pass through the channel, the compound (A) and the compound (B) that are far remote from each other have less occasion of contact and are hard to be reacted. Consequently, only the compound (A) and the compound (B) that are in the vicinity of each other are reacted, but the reaction does not proceed even when the compounds further migrate inside the channel. The inventors have found that when the mixed liquid of the compound (A) and the compound (B) having an isocyanate group is caused to pass through the tubular microchannel having a space size making a fluid cross-sectional area, through which a liquid passes densely, of from 0.1 to 4.0 mm$^2$ in such a manner that provides a Reynolds number in a range of from 0.2 to 300, such a state is formed in the channel that mixture proceeds associated with a microturbulent flow, thereby activating contact between the compound (A) and the compound (B), and thus the inventors have completed the invention. The Reynolds number is preferably from 3 to 200, and more preferably from 5 to 150. In the case where the Reynolds number is less than 0.2, the reaction proceeds too slowly to cause gelation due to the prolonged residence time, and the Reynolds number exceeding 300 is not preferred since the enhancement of the reaction efficiency is limited, and the reaction device becomes too long.

The Reynolds number referred in the invention is calculated by the following expression (1).

$$\text{Reynolds number} = (D \times u \times \rho)/\mu \qquad (1)$$

Herein, D is the inner diameter of the channel, u is the average flow velocity, $\rho$ is the density of the fluid, and $\mu$ is the viscosity of the fluid. In the invention, the terms in the expression (1) are defined as follows for providing the Reynolds number.

D (inner diameter of channel): equivalent diameter of the tubular microchannel (m), wherein the equivalent diameter is ((4× cross-sectional area of tubular microchannel (m$^2$))/ perimeter (m))

u (average flow velocity): flow velocity (m/sec) of the mixed liquid of the compound (A) and the compound (B)

$\rho$ (density of fluid): density of hydroxypropyl acrylate at 20° C. (1,000 kg/m$^3$)

$\mu$ (viscosity of fluid): viscosity of hydroxypropyl acrylate at 20° C. (4 mPa·s)

In the process for producing a urethane (meth)acrylate of the invention, it is necessary to heat the heat-conducting reaction device to a temperature of from 100 to 250° C. Such an advantageous effect is obtained by selecting the temperature that the reaction between the hydroxyl group and the isocyanate group is performed with good efficiency while preventing runaway reaction, which is polymerization of the (meth)acryloyl group, from occurring. The temperature of the heat-conducting reaction device is preferably from 140 to 210° C., and more preferably from 160 to 190° C., since the runaway reaction is hard to occur, and a good production efficiency is obtained.

In the process for producing a urethane (meth)acrylate of the invention, the cross-sectional area of the fluid passing the microchannel of the reaction device used in the invention, the Reynolds number of the mixed liquid passing through the microchannel, and the temperature of the heat-conducting reaction device are selected in the aforementioned manners, whereby the hydroxyl group and the isocyanate group undergo efficient reaction, and consequently, a urethane (meth)acrylate thus produced can be cooled before occurrence of reaction of the (meth)acryloyl groups. The flow velocity upon causing the mixed liquid to pass through the microchannel is preferably from $0.9 \times 10^{-4}$ to 4.2 m/sec, and more preferably from $1.5 \times 10^{-2}$ to 1.5 m/sec.

In the invention, a urethane (meth)acrylate can be produced without the use of a catalyst. For example, a heavy metal-free urethane (meth)acrylate or the like can be produced by using no catalyst. Furthermore, for example, such a problem can be avoided that a urethane (meth)acrylate produced with a catalyst is colored.

The heat-conducting reaction device used in the invention is not particularly limited in other requirements than that the reaction device has a heat exchange function and has a tubular microchannel having a space size making a fluid sectional area, through which a liquid passes densely, of from 0.1 to 4.0 mm$^2$. Examples of the reaction device include a device having the aforementioned channel (which may be hereinafter referred simply to as "microchannel") in a member, which is used as a device for chemical reaction.

The cross-sectional shape obtained by cutting perpendicularly the flow of the mixed liquid containing the compound (A) and the compound (B) in the tubular microchannel may be a square shape, a rectangular shape, a trapezoidal or parallelogram shape, a triangular shape, a polygonal shape including a pentagonal shape (including a shape obtained by rounding the corners thereof and a shape having a high aspect ratio, i.e., a slit shape), an astral shape, and a circular shape including a hemicircular shape and an elliptical shape, or the like. The cross-sectional shape of the microchannel may not be necessarily constant thereover.

The method for forming the tubular microchannel is not particularly limited, and in general is formed in such a manner that a member (X) having a trench formed on a surface thereof is fixed through the surface having the trench to another member (Y) by lamination, adhesion or the like, thereby forming the microchannel as a space between the member (X) and the member (Y).

In the case where the tubular microchannel is formed between the member (X) and the member (Y), the member (X) may have a heat exchange function. For example, a trench, through which a temperature controlling liquid flows, is formed on the surface of the member (X), and another member is fixed to the surface having the trench, through which a temperature controlling liquid flows, by adhesion, lamination or the like. In general, the member (X) having a trench on the surface thereof and the member (Y) having a trench, through which a temperature controlling liquid flows, are adhered through the surface having the trench of the member (X) and the surface of the member (Y) opposite to the surface having the trench fixed to each other, thereby forming the channel, and the plural members (X) and the plural members (Y) are fixed alternately to each other.

In this case, the trench may be formed as a dent having a height lower than the surrounding or may be formed as a gap between walls standing on the surface of the member. The trench may be formed on the surface of the member in an arbitrary method, and examples of the method that can be employed include an injection molding method, a solvent casting method, a melt replication method, cutting, etching, photolithograph (including energy ray lithography), and laser abrasion.

The layout of the channel in the member may be linear, branched, comb form, curve, spiral, zigzag or any other arbitrary arrangement depending on purposes.

The channel may be connected, for example, to a mixing field, an extraction field, a separation field, a flow rate measuring part, a detecting part, a liquid storage tank, a membrane separation mechanism, a connection port to the inside or outside of the device, a connection path, an expansion path of chromatography or cataphoresis, a part of a valve mechanism (a peripheral part of a valve), a pressurizing mechanism and a depressurizing mechanism.

The outer shape of the member is not particularly limited and may be any shape depending on purposes. Examples of the shape of the member include a plate shape, a sheet shape (including a film shape, a ribbon shape and the like), a coated film shape, a bar shape, a tube shape and another molded material having a complicated shape. The outer dimension including the thickness and the like is preferably constant thereover. An arbitrary material may be used for the member, and examples thereof include a polymer, glass, ceramics, a metal and a semiconductor.

The heat-conducting reaction device used in the invention is preferably such one that is produced by fixing the member (X) having a trench on the surface thereof with the other member (Y) on the surface having the trench by lamination, adhesion or the like, thereby forming the tubular microchannel as a space between the member (X) and the member (Y). Examples of the heat-conducting reaction device include such one that has a structure containing plural heat-conducting plate structures each having plural trenches on the surface thereof, which are laminated on each other.

The channel formed in the aforementioned manner is a space formed between the members by combining at least two members, and in alternative, a simple tube or a member having a tubular shape may be used as the reaction channel. The length of the channel may be appropriately determined for providing a desired reaction rate, and is generally from 0.5 to 100 m, and preferably from 3 to 70 m.

Examples of the heat-conducting reaction device used in the production process of the invention include such a device that is produced by laminating alternately a heat-conducting plate structure having the tubular microchannel provided therein and a heat-conducting plate structure having a channel, through which a liquid for heat exchanging with the mixed liquid passes. A mixing space for mixing the compound (A) and the compound (B) separately fed may be provided preceding or inside the reaction device. It is preferred in the invention that the compound (A) and the compound (B) are preferably fed as a mixed liquid formed by mixing in advance to the heat-conducting reaction device continuously.

Figure 1:
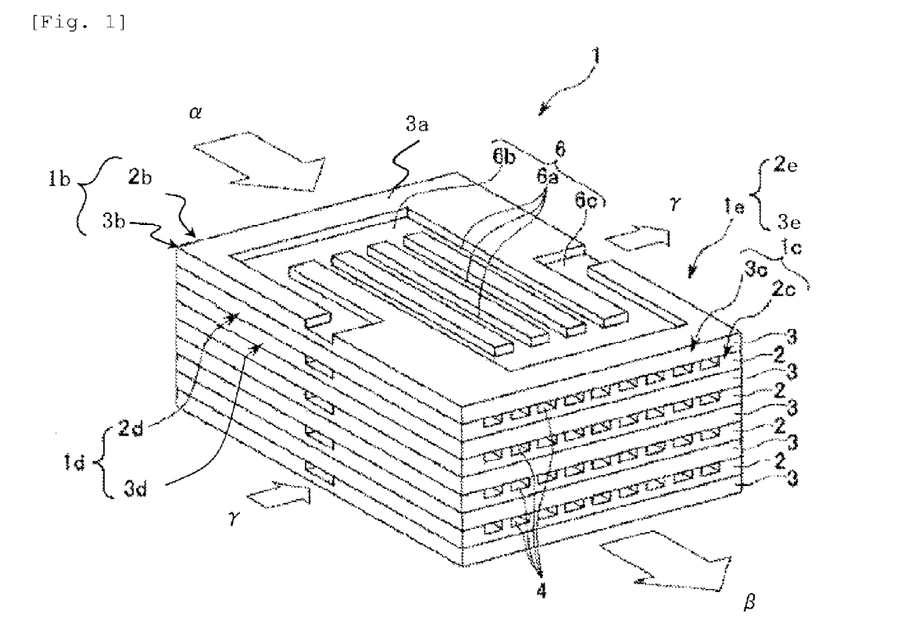
FIG. 1 The figure is a perspective view showing the schematic overall structure of the chemical reaction device including the connecting part used in the production process of the invention.

The heat-conducting reaction device having the tubular microchannel formed inside used in the invention will be specifically described below. FIG. 1 is a schematic illustration showing an example of a chemical reaction device 1 having a tubular microchannel having a space size making a fluid sectional area, through which a liquid passes densely, of from 0.1 to 4.0 $mm^2$, which is a reaction device containing plates each having the tubular microchannel, through which the mixed liquid passes, and plates each having a channel, through which a liquid for heat exchanging with the mixed liquid passes, laminated alternately.

Figure 2:
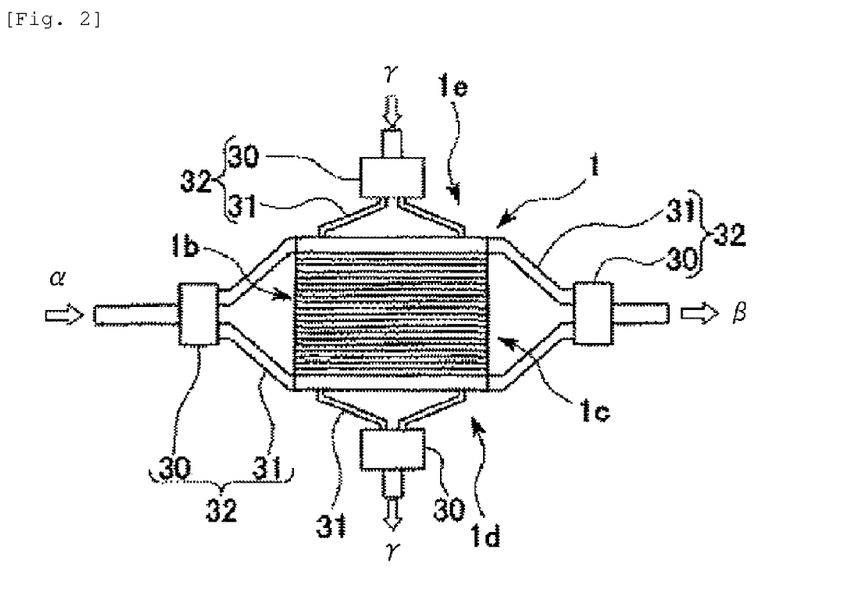
FIG. 2 The figure is a horizontal cross-sectional view showing the schematic overall structure of the chemical reaction device including the connecting part used in the production process of the invention.

The chemical reaction device 1 in FIG. 1 is constituted by laminating alternately plural first plates (2 in FIG. 1) and plural second plates (3 in FIG. 1) having the same rectangular plate shape. Each one of the first plates have a channel having the cross-sectional area of from 0.1 to 4.0 ($mm^2$) (which is referred hereinafter to as a reaction channel) (hereinafter, the plate having the reaction channel is referred to as a process plate). The second plate has a channel for a temperature controlling liquid (which is hereinafter referred to as a temperature controlling channel) (the plate having the temperature controlling channel is hereinafter referred to as a temperature controlling plate). As shown in FIG. 2, inlet ports and outlet ports thereof are disposed by scattering in each areas including the end surfaces $1b$ and $1c$ and the side surfaces $1d$ and $1e$ of the chemical reaction device 1, and connecting parts 32 each containing a connector 30 and a joint part 31 are connected to the areas for causing the compound (A) and the compound (B), and the temperature controlling liquid to pass through, respectively.

Through the connecting parts, a liquid α(mixed liquid) containing the compound (A) and the compound (B) is fed to the end surface $1b$, a liquid β containing a reaction product between the compound (A) and the compound (B) is discharged from the end surface $1c$, and the temperature controlling liquid γ is fed to the side surface $1e$ and discharged from the side surface $1d$.

The shape in plane view of the chemical reaction device 1 is not limited to the rectangular shape as shown in the figure, and may be a square shape or a rectangular shape having a longer distance between the side surfaces $1d$ and $1e$ than the distance between the end surfaces $1b$ and $1c$. In the following description, for simplification, the direction from the end surface $1b$ toward the end surface $1c$ refers to the longitudinal direction of the process plates and the temperature controlling plates of the chemical reaction device 1, and the direction from the side surface $1d$ toward the side surface $1e$ refers to the transverse direction of the process plates and the temperature controlling plates of the chemical reaction device 1, according to the configuration shown in the figure.

Figure 3:
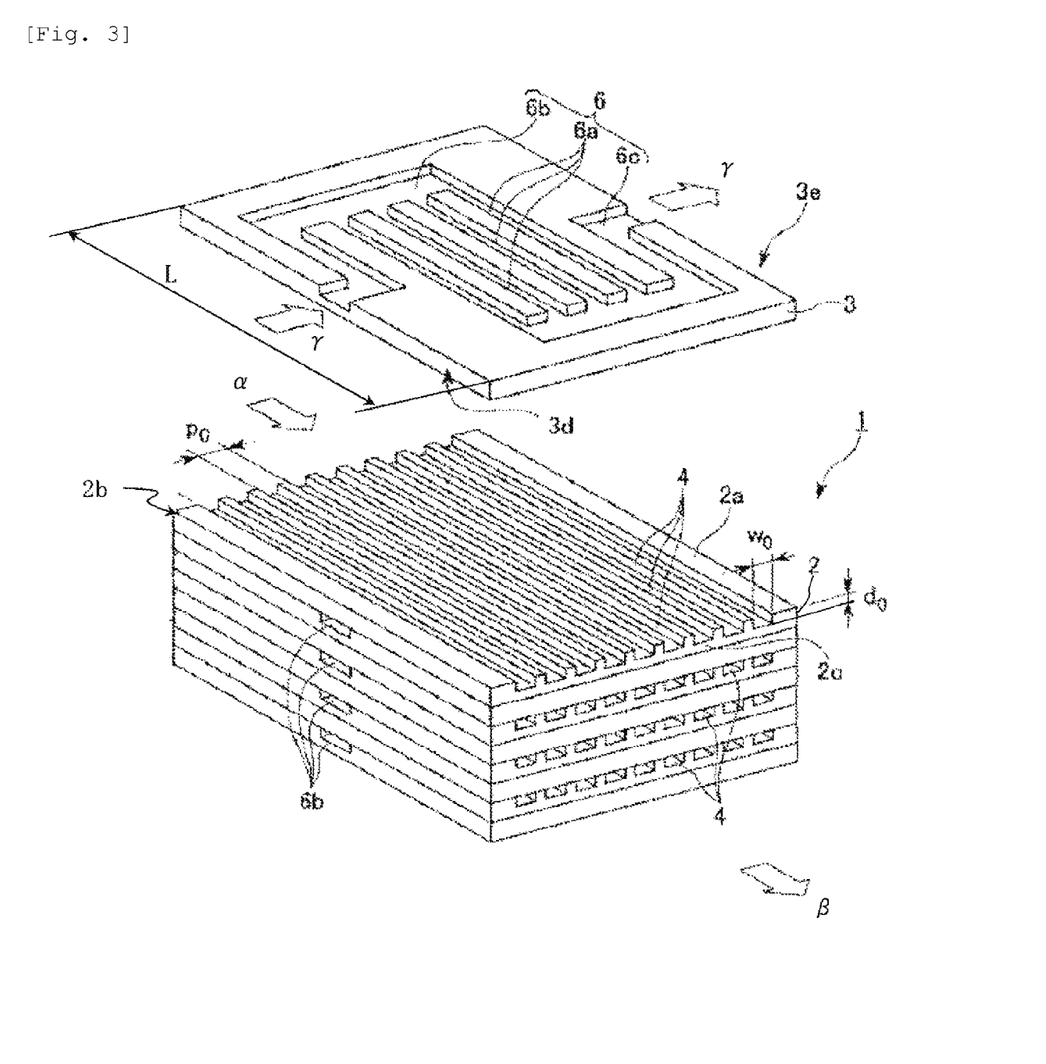
FIG. 3 The figure is a perspective exploded view showing the structures of the two kinds of plates in FIG. 2.

As shown in FIG. 3, the process plate has on one surface $2a$ thereof plural channels 4 each having a concave trench cross-sectional shape that penetrate in the longitudinal direction of the process plate and are arranged in the transverse direction with a prescribed interval $p_0$. The length of the channel 4 is designated as L. The cross-sectional shape has a width $w_0$ and a depth $d_0$.

The cross-sectional shape of the channel 4 can be appropriately determined corresponding to the kind and the flow rate of the liquid α containing the compound (A) and the compound (B) and the length L of the channel, and the width $w_0$ and the depth $d_0$ are set in a range of from 0.1 to 16 (mm) and a range of from 0.1 to 2 (mm), respectively, for ensuring homogeneity of the temperature distribution within the cross section thereof. The values of the width and the depth mentioned are those disclosed in the figure, and can be appropriately interpreted to make a wider value with respect to the heat-conducting surface. The number of channels is not particularly limited and is, for example, from 1 to 1,000, and preferably from 10 to 100, per one plate.

The liquid α are caused to flow within each of the channels 4, and as shown in FIGS. 1 to 3, is fed from the side of the one end surface 2b and discharged to the side of the other end surface 2c.

As shown in FIG. 1, the temperature controlling plate has on one surface 3a thereof temperature controlling channels 6 each having a concave trench cross-sectional shape provided with a prescribed distance. The cross-sectional area of the temperature controlling channel 6 is not particularly limited as far as heat can be conducted to the reaction channels and is generally in a range approximately from 0.1 to 4.0 (mm$^2$), and more preferably from 0.3 to 1.0 (mm$^2$). The number of the temperature controlling channels 6 may be appropriately determined in consideration of the heat exchange efficiency without particular limitation, and is, for example, from 1 to 1,000, and preferably from 10 to 100, per one plate.

As shown in FIGS. 1 and 3, the temperature controlling channel 6 may contain plural main channels 6a disposed along the longitudinal direction of the temperature controlling plate, and a feed-side channel 6b and a discharge-side channel 6c disposed on the upstream side and the downstream side of the main channels 6a, respectively, substantially perpendicular to the channels 4 and connected to the main channels 6a. In FIGS. 1 and 3, the feed-side channel 6b and the discharge-side channel 6c each are turned at a right angle twice and are opened to the outside at the side surfaces 3d and 3e of the temperature controlling plate, respectively. With respect to the number of the channels of the temperature controlling channel 6, plural channels are disposed only for the main channels 6a of the temperature controlling channel 6, and the feed-side channel 6b and the discharge-side channel 6c each are constituted by only one channel.

The main channels 6a of the temperature controlling channel 6 are provided in the transverse direction of the temperature controlling plate with respect to the channels 4 in an area overlapping in the lamination direction the area where the channels 4 are distributed.

It is preferred that the main channels 6a are each disposed in the lamination direction between the channels 4 and 4 adjacent to each other, and it is more preferred that the main channels 6a are each disposed to overlap in the lamination direction each of the channels 4.

The plural process plates and the plural temperature controlling plates are laminated and fixed alternately with the process plates and the temperature controlling plate being in the same direction.

In the embodiment of the chemical reaction device 1, accordingly, the channels 4 and the temperature controlling channels 6 are covered with the lower surface of the plate laminated with the open surface of a concave trench thereof upward, thereby forming a tunnel shape having a rectangular cross section with both ends open.

The process plates and the temperature controlling plates may be produced with an appropriate metallic material, and for example, can be produced by etching a stainless steel plate to form the channels 4, the temperature controlling channels 6 and the like, and subjecting the surface of the channels to electrolytic polishing.

Figure 4:
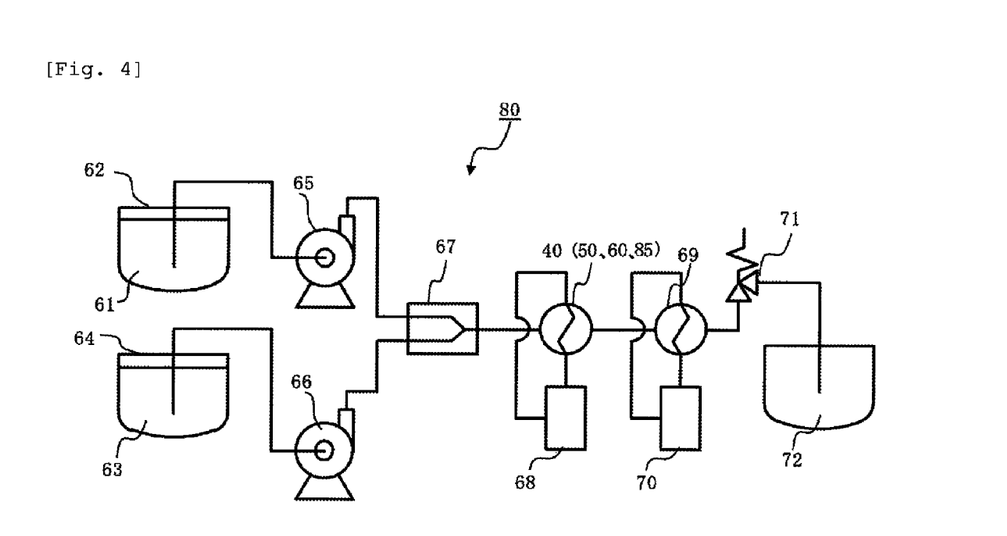
FIG. 4 The figure is a schematic structural view showing schematically the production apparatus used in Examples and Comparative Examples.

Examples of an apparatus that is equipped with a chemical reaction device having the channels used in the production process of the invention include a production apparatus shown in FIG. 4. Specifically, a production apparatus having a chemical reaction device shown below is exemplified.

Chemical Reaction Device

The chemical reaction device has the structure shown in FIG. 1, and the structure contains process plates and temperature controlling plates laminated alternately. The process plates each have channels 4 formed therein, and the temperature controlling plates each have temperature controlling channels 6 formed therein.

The chemical reaction device 40 used in the production apparatus shown in FIG. 4 contains 20 plies of process plates each having 21 reaction channels 4 formed by dry etching and 21 plies of temperature controlling plates each having 21 temperature controlling channels 6 formed by dry etching laminated alternately. The process plates 2 and the temperature controlling plates 3 each are formed of SUS304 as a material, and each have a thickness of 1 mm. The reaction channels 4 and the temperature controlling channels 6 each have a cross sectional dimension of 1.2 mm in width and 0.5 mm in depth.

The chemical reaction device 50 used in the production apparatus shown in FIG. 4 contains 2 plies of process plates each having 5 reaction channels 4 formed by dry etching and 3 plies of temperature controlling plates each having 5 temperature controlling channels 6 formed by dry etching laminated alternately. The process plates 2 and the temperature controlling plates 3 each are formed of SUS304 as a material, and each have a thickness of 1 mm. The reaction channels 4 and the temperature controlling channels 6 each have a cross sectional dimension of 1.2 mm in width and 0.5 mm in depth.

The chemical reaction device 60 used in the production apparatus shown in FIG. 4 contains 4 plies of process plates each having 5 reaction channels 4 formed by dry etching and 5 plies of temperature controlling plates each having 5 temperature controlling channels 6 formed by dry etching laminated alternately. The process plates 2 and the temperature controlling plates 3 each are formed of SUS304 as a material, and each have a thickness of 1 mm. The reaction channels 4 and the temperature controlling channels 6 each have a cross sectional dimension of 1.2 mm in width and 0.5 mm in depth.

The chemical reaction device 85 used in the production apparatus shown in FIG. 4 contains 6 plies of process plates each having 10 reaction channels 4 formed by dry etching and 7 plies of temperature controlling plates each having 10 temperature controlling channels 6 formed by dry etching laminated alternately. The process plates 2 and the temperature controlling plates 3 each are formed of SUS304 as a material, and each have a thickness of 1 mm. The reaction channels 4 and the temperature controlling channels 6 each have a cross sectional dimension of 1.2 mm in width and 0.5 mm in depth. The reaction channels 4 each have a length of 80 mm.

In FIG. 4, an outlet port of a tank 62 (i.e., a first tank) for storing the compound (A) (61) is connected to an inlet port of a plunger pump 65 through a pipe, through which the compound (A) flows, and an outlet port of a tank 64 (i.e., a second tank) for storing the compound (B) is connected to an inlet port of a plunger pump 66 through a pipe, through which the compound (B) (63) flows. Pipes, through each of which the compound (A) and the compound (B) are caused to flow with the plunger pump 65 and the plunger pump 66 respectively, are extended from an outlet port of the plunger pump 65 and an outlet port of the plunger pump 66, respectively, and the pipes are connected to an inlet port of a mixer (i.e., a mixing space for mixing the compound (A) and the compound (B)) 67.

The compound (A) (61) and the compound (B) (63) are mixed in the mixer 67, thereby forming a mixed liquid containing the compound (A) (61) and the compound (B) (63). The liquid moves to an inlet port 1b of the chemical reaction device 40, 50, 60 or 85 through a pipe connected to an outlet port of the mixer 67. A temperature controlling unit 68 is connected to the chemical reaction device 40, 50, 60 or 85. The compound (A) and the compound (B) in the liquid α are reacted with each other while moving in the microchannel of the chemical reaction device 40, 50, 60 or 85. The liquid moves within the microchannel of the chemical reaction device 40, 50, 60 or 85 and reaches an outlet port lc of the chemical reaction device 40, 50, 60 or 85. Thereafter, the liquid moves to an inlet port of a cooling heat exchange device 69 through a pipe connected to the outlet port.

In the production process of the invention, the reaction is preferably performed by using a reaction device containing plural heat-conducting reaction devices connected in series each having a tubular microchannel formed therein, such as the chemical reaction device 40, 50, 60 or 85, since the Reynolds number and the temperature can be respectively changed.

After providing a urethane (meth)acrylate in the aforementioned manner, the reaction product obtained is discharged from the heat-conducting reaction device. The reaction product is then cooled continuously, under a temperature condition of preferably from 50 to 90 ° C., more preferably 70° C. The reaction product is cooled quickly and continuously, thereby preventing runaway reaction of the (meth)acryloyl group from occurring. The cooling operation may be performed by natural air cooling in the air, by placing the discharged product quickly in a solvent for cooling, or by causing the product to pass through a cooling device having a heat exchange function. It is preferred in the invention that the product is preferably cooled by causing to pass through a cooling device having a heat exchange function. The cooling device is preferably a cooling heat exchange device having a tubular microchannel formed therein.

The continuous cooling operation with the cooling heat exchange device is preferably performed, for example, by causing the reaction product to pass continuously through the cooling heat exchange device having a tubular microchannel formed therein connected to the exit of the reaction liquid (i.e., the outlet port) of the heat-conducting reaction device.

Specifically, the liquid β containing the reaction product of the compound (A) (61) and the compound (B) (62) (i.e., a urethane (meth)acrylate) moving to an inlet port of the cooling heat exchange device (i.e., the cooling device) 69 is cooled while moving in the cooling heat exchange device 69, and reaches an outlet port of the cooling heat exchange device 69. The liquid β is discharged from the cooling heat exchange device 69 through a pipe connected to the outlet port and then discharged to a receiving vessel 72 through a valve 71.

Preferred examples of the cooling heat exchange device used in the invention include a heat-conducting reaction device having a tubular microchannel formed therein, which is preferably used as the heat-conducting reaction device, i.e., one having plural heat-conducting plate structures each having plural trenches formed on the surface thereof laminated on each other. Examples of the apparatus include an apparatus having the chemical reaction device.

The reaction between the compound (A) and the compound (B) in the tubular microchannel may be terminated at an arbitrary yield, and the reaction product and the unreacted materials may be discharged to the outside of the reaction channel. In general, a higher yield increases the viscosity of the reaction product, thereby increasing the pressure loss and decreasing the flow velocity. Accordingly, such an operation may be employed that the reaction until the initial stage or the intermediate stage of reaction, for example, providing a Reynolds number of 0.2 or more, and more preferably from 3 to 200, is performed by the production process of the invention, and subsequently, the composition containing the unreacted materials is placed in a vessel or a storage tank for batch reaction or placed in a channel having a larger cross-sectional area, thereby reacting the remaining unreacted materials.

The compound (A) and the compound (B) used in the production process of the invention each may be a liquid having a viscosity capable of being fed, and may be heated or dissolved in and diluted with a solvent for enabling the feeding.

The compound (A) and the compound (B) each may contain, depending on necessity, an additive, such as a catalyst (initiator) and a polymerization inhibitor in such an extent that the channel is not clogged.

The compound (A) and the compound (B) used in the invention may be fed to the channel individually or in a mixed state as far as the reaction is adversely affected. The compounds may be diluted with a solvent and may contain an additive, such as a catalyst (initiator) and a polymerization inhibitor, depending on necessity.

The catalyst (initiator) is not particularly limited as far as it can be dissolved in the compound (A) and the compound (B) or dispersed therein in such an extent that the channel is not clogged, or can be used after dissolving in a solvent, and a known catalyst (initiator) may be used, examples of which include a metallic catalyst, such as dibutyltin diacetate and dibutyltin dilaurate.

The polymerization inhibitor is not particularly limited as far as it can be dissolved in the compound (A) and the compound (B) or dispersed therein in such an extent that the channel is not clogged, or can be used after dissolving in a solvent, and a known polymerization inhibitor may be used, examples of which include methoquinone and hydroquinone.

EXAMPLE

The invention will be described in more detail with reference to examples below. The percentages in the examples are by weight unless otherwise indicated.

Chemical Reaction Device used in Examples and Comparative Examples

A chemical reaction device having the structure shown in FIG. 1 was used in the example. The structure contains process plates 2 and temperature controlling plates 3 laminated alternately. The process plates each have a channel 4 formed therein, and the temperature controlling plates each have a temperature controlling channel 6 formed therein. As the chemical reaction device, chemical reaction devices 40, 50, 60 and 85 shown in FIG. 4 exhibiting different Reynolds numbers on the same flow rate (on the same flow velocity) were used.

The chemical reaction device 40 contains 20 plies of process plates each having 21 reaction channels 4 formed by dry etching and 22 plies of temperature controlling plates each having 21 temperature controlling channels 6 formed by dry etching laminated alternately. The process plates 2 and the temperature controlling plates 3 each are formed of SUS304 as a material, and each have a thickness of 1 mm. The reaction channels 4 and the temperature controlling channels 6 each have a cross sectional dimension of 1.2 mm in width and 0.5 mm in depth. The reaction channels 4 each have a length of 198 mm.

The chemical reaction device 50 contains 2 plies of process plates each having 5 reaction channels 4 formed by dry etching and 3 plies of temperature controlling plates each having 5 temperature controlling channels 6 formed by dry etching laminated alternately. The process plates 2 and the temperature controlling plates 3 each are formed of SUS304 as a material, and each have a thickness of 1 mm. The reaction channels 4 and the temperature controlling channels 6 each have a cross sectional dimension of 1.2 mm in width and 0.5 mm in depth. The reaction channels 4 each have a length of 40 mm.

The chemical reaction device 60 contains 4 plies of process plates each having 5 reaction channels 4 formed by dry etching and 5 plies of temperature controlling plates each having 5 temperature controlling channels 6 formed by dry etching laminated alternately. The process plates 2 and the temperature controlling plates 3 each are formed of SUS304 as a material, and each have a thickness of 1 mm. The reaction channels 4 and the temperature controlling channels 6 each have a cross sectional dimension of 1.2 mm in width and 0.5 mm in depth. The reaction channels 4 each have a length of 40 mm.

The chemical reaction device 85 contains 6 plies of process plates each having 10 reaction channels 4 formed by dry etching and 7 plies of temperature controlling plates each having 10 temperature controlling channels 6 formed by dry etching laminated alternately. The process plates 2 and the temperature controlling plates 3 each are formed of SUS304 as a material, and each have a thickness of 1 mm. The reaction channels 4 and the temperature controlling channels 6 each have a cross sectional dimension of 1.2 mm in width and 0.5 mm in depth. The reaction channels 4 each have a length of 80 mm.

The cooling heat exchange device 69 contains 20 plies of process plates each having 21 reaction channels 4 formed by dry etching and 22 plies of temperature controlling plates each having 21 temperature controlling channels 6 formed by dry etching laminated alternately. The process plates 2 and the temperature controlling plates 3 each are formed of SUS304 as a material, and each have a thickness of 1 mm. The reaction channels 4 and the temperature controlling channels 6 each have a cross sectional dimension of 1.2 mm in width and 0.5 mm in depth. The reaction channels 4 each have a length of 198 mm.

Example 1

2-Hydroxypropyl acrylate (HPA) 61 (2.1 mol) and tolylene diisocyanate (TDI) 63 (1.0 mol) were mixed and reacted by using a production apparatus 80 shown in FIG. 4 having one chemical reaction device 40 connected. 50 ppm of dibutyltin diacetate as a catalyst and 200 ppm of hydroquinone as an inhibitor were mixed and dissolved in HPA 61 in advance.

HPA 61 in the first tank 62 and TDI 63 in the second tank 64 were continuously fed with the plunger pumps 65 and 66 as a mixed liquid containing HPA 61 and TDI 63 having a molar ratio of 2.1/1.0 to the mixer (mixing space) 67, the chemical reaction device 40, the cooling heat exchange device 69 and the exhaust pressure valve 71 to make a Reynolds number of 0.275 (flow velocity: $1.6 \times 10^{-3}$ m/sec), and the reaction mixture thus discharged was received by the receiving vessel 72. In the mixer, HPA and TDI were mixed. In the chemical reaction device 40, a temperature controlling liquid (oil) at 120° C. was caused to flow continuously through the temperature controlling channel 6 of the temperature controlling plate by the temperature controlling unit 68. In the cooling heat exchange device 69, warm water at 70° C. was caused to flow continuously by the temperature controlling unit 70. The reaction was performed at a pressure in the tube of 1 MPa or more controlled by the exhaust pressure valve 71.

The result of quantitative determination of the unreacted isocyanate groups in the reaction mixture revealed that urethane acrylate was formed at a reaction rate of 65% with a reaction time of 120 seconds. No runaway reaction occurred. The reaction time referred herein means a period of time of from the time when the mixed liquid of the compound (A) and the compound (B) is fed to the end surface of the chemical reaction device to the time when the reaction mixture is discharged from the end surface of the cooling heat exchange device.

The reaction mixture thus discharged exhibited a reaction rate of 65%, and contained a large amount of the raw materials of the resulting urethane acrylate. Accordingly, the weight average molecular weight of the urethane acrylate was not measured.

Example 2

HPA 61 (2.1 mol) and TDI 63 (1.0 mol) were mixed and reacted by using a production apparatus 80 shown in FIG. 4 having 10 chemical reaction devices 50 connected in series. 50 ppm of dibutyltin diacetate as a catalyst and 200 ppm of hydroquinone as an inhibitor were mixed and dissolved in HPA 61 in advance.

HPA 61 in the first tank 62 and TDI 63 in the second tank 64 were continuously fed with the plunger pumps 65 and 66 as a mixed liquid containing HPA 61 and TDI 63 having a molar ratio of 2.1/1.0 to the mixer 67, the chemical reaction devices 50, the cooling heat exchange device 69 and the exhaust pressure valve 71 to make a Reynolds number of 6 (flow velocity: $3.5 \times 10^{-2}$ m/sec), and the reaction mixture thus discharged was received by the receiving vessel 72. In the mixer, HPA and TDI were mixed. In the chemical reaction devices 50, a temperature controlling liquid (oil) at 180° C. was caused to flow continuously through the temperature controlling channel 6 of the temperature controlling plate by the temperature controlling unit 68. The temperature of the reaction mixture in the chemical reaction devices was measured at 10 positions where the devices were divided into 10 along the channel. In the cooling heat exchange device 69, warm water at 70° C. was caused to flow continuously by the temperature controlling unit 70. The reaction was performed at a pressure in the tube of 1 MPa or more controlled by the exhaust pressure valve 71.

Figure 5:
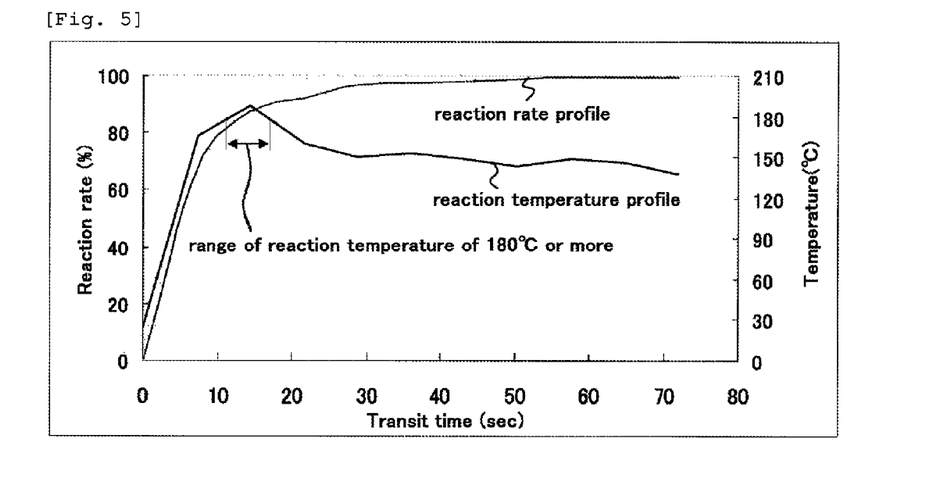
FIG. 5 The figure is a graph showing the experimental results of the reaction rate and the reaction temperature with respect to the transit time in Example 2.

In the reaction process, the reaction mixture in the chemical reaction devices was measured for temperature and reaction rate of HPA and TDI at 10 positions where the devices were divided into 10 along the channel. The temperatures and the reaction rates of HPA and TDI of the reaction mixture at the times when the reaction mixture passes the positions (transit time) are shown in FIG. 5. The transit time herein means a period of time of from the time when the mixed liquid of HPA and TDI is fed to the end surface of the chemical reaction device to the time when it is discharged from the end surface thereof, and means the reaction time.

The reaction rate was 99.7% with a transit time (reaction time) of 50 seconds, and thus the reaction was substantially completed. The period where the temperature of the reaction mixture exceeded 180° C., the temperature of the temperature controlling liquid, due to the reaction heat was several seconds or less, and the temperature of the reaction product became 180° C. or less owing to the high heat removal capability of the chemical reaction devices. Accordingly, no runaway reaction occurred at such a reaction temperature that had not been achieved by a reaction vessel, and the reaction time was shortened to such an extent that had not been achieved by a reaction vessel.

The urethane (meth)acrylate compound had a weight average molecular weight of 594. The measurement of a weight average molecular weight was performed by using HLC-8120 GPC, produced by Tohso Corporation, equipped with a refractive index detector (RI) as a detector and TSK gel G1000HXL+G2000HXL+G3000HXL+G4000HXL as columns for measurement. The measurement conditions were tetrahydrofuran (THF) as a solvent, a concentration of a specimen controlled to a range of from 0.2 to 0.3%, a column temperature of 40° C. and a flow velocity of 1.0 ml/min.

Example 3

(Production of Urethane Acrylate)

HPA 61 (2.1 mol) and TDI 63 (1.0 mol) were mixed and reacted by using a production apparatus 80 shown in FIG. 4 having 20 chemical reaction devices 60 connected in series. 50 ppm of dibutyltin diacetate as a catalyst and 200 ppm of hydroquinone as an inhibitor were mixed and dissolved in HPA 61 in advance.

HPA 61 in the first tank 62 and TDI 63 in the second tank 64 were continuously fed with the plunger pumps 65 and 66 as a mixed liquid containing HPA 61 and TDI 63 having a molar ratio of 2.1/1.0 to the mixer 67, the chemical reaction devices 60, the cooling heat exchange device 69 and the exhaust pressure valve 71 to make a Reynolds number of 50 (flow velocity: $2.8 \times 10^{-1}$ m/sec), and the reaction mixture thus discharged was received by the receiving vessel 72. In the mixer, HPA and TDI were mixed. In the chemical reaction devices 60, a temperature controlling liquid (oil) at 180° C. was caused to flow continuously through the temperature controlling channel 6 of the temperature controlling plate by the temperature controlling unit 68. In the cooling heat exchange device 69, warm water at 70° C. was caused to flow continuously by the temperature controlling unit 70. The reaction was performed at a pressure in the tube of 1 MPa or more controlled by the exhaust pressure valve 71. The period of time (reaction time) of from the time when the mixed liquid of HPA and TDI was fed to the end surface of the chemical reaction device 60 to the time when it was discharged from the end surface of the cooling heat exchange device was 20 seconds.

The result of quantitative determination of the unreacted isocyanate groups in the reaction mixture revealed that urethane acrylate was formed at a reaction rate of 97% with a reaction time of 20 seconds. No runaway reaction occurred.

Example 4

A reaction mixture was obtained in the same manner as in Example 3 except that the mixed liquid of HPA 61 and TDI 63 was caused to flow to make a Reynolds number of 250 (flow velocity: 1.41 m/sec), and in the production apparatus 80 shown in FIG. 4, 50 chemical reaction devices 60 were connected in series. The period of time (reaction time) of from the time when the mixed liquid of HPA and TDI was fed to the end surface of the chemical reaction device 60 to the time when it was discharged from the end surface of the cooling heat exchange device was 4 seconds. The result of quantitative determination of the unreacted isocyanate groups in the reaction mixture revealed that urethane acrylate was formed at a reaction rate of 80% with a reaction time of 4 seconds. No runaway reaction occurred.

Example 5

HPA 61 (2.1 mol) and TDI 64 (1.0 mol) were mixed and reacted by using a production apparatus 80 shown in FIG. 4 having 5 chemical reaction devices 85 connected in series. 200 ppm of hydroquinone as an inhibitor was mixed and dissolved in HPA 61 in advance.

Example 5

HPA (2.1 mol) and TDI 63 (1.0 mol) were mixed and reacted by using a production apparatus 80 shown in FIG. 4 having 5 chemical reaction devices 85 connected in series. 200 ppm of hydroquinone as an inhibitor was mixed and dissolved in HPA 61 in advance.

HPA 61 in the first tank 62 and TDI 63 in the second tank 64 were continuously fed with the plunger pumps 65 and 66 as a mixed liquid containing HPA 61 and TDI 63 having a molar ratio of 2.1/1.0 to the mixer 67, the chemical reaction devices 85, the cooling heat exchange device 69 and the exhaust pressure valve 71 to make a Reynolds number of 1.0 (flow velocity: $5.8 \times 10^{-3}$ m/sec), and the reaction mixture thus discharged was received by the receiving vessel 72. In the mixer, HPA and TDI were mixed. In the chemical reaction devices 85, a temperature controlling liquid (oil) at 180° C. was caused to flow continuously through the temperature controlling channel 6 of the temperature controlling plate by the temperature controlling unit 68. In the cooling heat exchange device 69, warm water at 70° C. was caused to flow continuously by the temperature controlling unit 70. The reaction was performed at a pressure in the tube of 1 MPa or more controlled by the exhaust pressure valve 71. The period of time (reaction time) of from the time when the mixed liquid of HPA and TDI was fed to the end surface of the chemical reaction device 85 to the time when it was discharged from the end surface of the cooling heat exchange device was 1,300 seconds.

The result of quantitative determination of the unreacted isocyanate groups in the reaction mixture revealed that urethane acrylate was formed at a reaction rate of 98% with a reaction time of 1,300 seconds. No runaway reaction occurred.

Comparative Example 1

A reaction mixture was obtained in the same manner as in Example 1 except that the mixed liquid of HPA 61 and TDI 63 was caused to flow at a flow velocity making a Reynolds number of 0.1 (flow velocity: $6.3 \times 10^{-4}$ m/sec). The period of time (reaction time) of from the time when the mixed liquid of HPA and TDI was fed to the end surface of the chemical reaction device 40 to the time when it was discharged from the end surface of the cooling heat exchange device was 300 seconds. Although no runaway reaction occurred, the reaction rate was only 40% with a reaction time of 300 seconds, and thus urethane acrylate was not able to be produced with good efficiency. The weight average molecular weight of the urethane acrylate was not measured.

Comparative Example 2

A reaction mixture was obtained in the same manner as in Example 1 except that the mixed liquid of HPA 61 and TDI 63 was caused to flow at a flow velocity making a Reynolds number of 0.05 (flow velocity: $3.0 \times 10^{-4}$ m/sec). The period of time (reaction time) of from the time when the mixed liquid of HPA and TDI was fed to the end surface of the chemical reaction device 40 to the time when it was discharged from the end surface of the cooling heat exchange device was 600 seconds. Although no runaway reaction occurred, the reaction rate was only 32% with a reaction time of 600 seconds, and thus urethane acrylate was not able to be produced with good efficiency. The weight average molecular weight of the urethane acrylate was not measured.

The temperature of the temperature controlling liquid for heating the chemical reaction device, the flow velocity, the Reynolds number, the reaction time and the reaction rate of the resulting urethane acrylate of Examples 1 to 5 and Comparative Examples 1 and 2 are shown in Table 1. It is apparent from Comparative Examples that when the Reynolds number is decreased, the reaction rate is lowered even though the reaction time is long, thereby failing to produce urethane acrylate with good efficiency. It is apparent from Examples that a larger Reynolds number increases the reaction speed, thereby producing urethane acrylate with good efficiency.

ing nozzle and an air blowing nozzle, and after mixing homogeneously, the content of the flask was heated to 60° C. After heating to 60° C., the heating operation was terminated, and 0.07 g of dibutyltin diacetate was charged. Immediately after charging dibutyltin diacetate, heat was generated uncontrollably, the temperature in the flask was increased to 240° C. over approximately 2 minutes and was finally increased to 330° C., the content of the flask was gelled, and a large amount of gas was generated from the flask.

The synthesis conditions in Comparative Examples 3 and 4 are shown in Table 2 along with the synthesis conditions in Example 2. The analysis values of the properties of the resulting urethane acrylate are shown in Table 3 along with the analysis value of the properties of Example 2.

TABLE 2

|  | Reaction mode | Reaction time | Temperature of liquid | Reynolds number in microchannel |
|---|---|---|---|---|
| Example 2 | continuous mode in microchannel | 50 seconds | 180° C. | 6.0 |
| Comparative Example 3 | batch mode in flask | 6.5 hours | 60-75° C. | — |
| Comparative Example 4 | batch mode in flask | 120 seconds | 60° C.->240° C. | — |

TABLE 1

|  | Example 1 | Example 2 | Example 3 | Example 4 | Example 5 | Comparative Example 1 | Comparative Example 2 |
|---|---|---|---|---|---|---|---|
| Chemical reaction device | 40 | 50 | 60 | 60 | 85 | 40 | 40 |
| Temperature of temperature controlling liquid (° C.) | 120 | 180 | 180 | 180 | 180 | 120 | 120 |
| Reynolds number | 0.275 | 6 | 50 | 250 | 1 | 0.1 | 0.05 |
| Flow velocity of mixed liquid (m/sec) | $1.6 \times 10^{-3}$ | $3.5 \times 10^{-2}$ | $2.8 \times 10^{-1}$ | 1.4 | $5.8 \times 10^{-3}$ | $6.3 \times 10^{-4}$ | $3.0 \times 10^{-4}$ |
| Reaction time (sec) | 120 | 50 | 20 | 4 | 1,300 | 300 | 600 |
| Reaction rate (%) | 65 | 99.7 | 97 | 80 | 98 | 40 | 32 |

Comparative Example 3

778 g of TDI, 0.24 g of hydroquinone and 0.07 g of dibutyltin diacetate were charged in a four-neck flask equipped with a thermometer, an agitator, a water-cooled condenser, a nitrogen blowing nozzle and an air blowing nozzle, and the content of the flask was heated to 60° C. After heating to 60° C., 1,236 g of HPA was added dropwise thereto over 2 hours, and after completing the dropwise addition, the temperature was increased to 75° C., followed by continuing the reaction at 75° C. for 3.5 hours. The reaction was terminated at the time when the remaining isocyanate group (NCO %) reached 0.1% or less, thereby providing urethane acrylate for comparison.

The weight average molecular weight of the urethane (meth)acrylate measured under the same measurement conditions was 598.

Comparative Example 4

783 g of TDI, 1,236 g of HPA and 0.24 g of hydroquinone were charged in a four-neck flask equipped with a thermometer, an agitator, a water-cooled condenser, a nitrogen blow-

TABLE 3

|  | Reaction rate % | Result of GPC measurement | Presence of runaway reaction |
|---|---|---|---|
| Example 2 | 99.7% | weight average molecular weight Mw: 594 | none |
| Comparative Example 3 | 99.7% | weight average molecular weight Mw: 598 | none |
| Comparative Example 4 | not measured | not measured | occurred gelation gas generated |

It is understood from the reaction conditions shown in Table 1 and the evaluation results shown in Table 2 that in Example 2, the reaction is completed in a considerably short period of time without occurrence of runaway reaction. This is a result obtained by such procedures that the compound (A) and the compound (B) are fed to the microchannel satisfying the particular conditions at the particular flow velocity, and reacted in the microchannel at the reaction temperature (180° C.), which cannot be generally employed by a batch mode reaction, such as a reaction vessel, due to danger of runaway reaction.

Comparative Examples 1 and 2 show the results obtained in such a manner that tolylene diisocyanate and 2-hydroxypropyl acrylate are fed to the particular microchannel at a velocity making a Reynolds number of less than 0.2, and reacted in the microchannel at the reaction temperature (120° C.), which cannot be generally employed by a batch mode reaction, such as a reaction vessel, due to danger of runaway reaction. It is understood that in the case where the Reynolds number is less than 0.2, even though the reaction is performed for a prolonged period of time at a considerably high reaction temperature, the viscosity of the reaction product is increased associated with the progress of the reaction to lower significantly the mixing property by molecular diffusion, and thus the reaction cannot be performed in a short period of time.

Comparative Example 3 shows the results of the batch mode performed with a reaction vessel. For the purpose of suppressing runaway reaction from occurring and controlling sufficiently the temperature in the system, 2-hydroxypropyl acrylate is fed by dropwise addition, and the reaction is performed at a low temperature of from 60 to 75° C., whereby a period of 6.5 hours is required until completion of the reaction. It is understood from the results that the results of Example 1 is a safe and efficient production process of a urethane (meth)acrylate compound.

Comparative Example 4 shows the results obtained in such a manner that 2-hydroxypropyl acrylate is also reacted by charging batchwise for shortening the reaction time. Immediately after adding the catalyst, heat is generated rapidly, and gelation occurs associated with severe generation of gas. So-called runaway reaction occurs. It is understood from the results that the results of Example 1 is a safe and efficient production process of a urethane (meth)acrylate compound.

EXPLANATION OF SYMBOLS

| | |
|---|---|
| α | liquid containing compound (A) and compound (B) |
| β | liquid containing reaction product of compound (A) and compound (B) |
| γ | temperature controlling liquid |
| 1 | chemical reaction device |
| 1b | end surface of chemical reaction device |
| 1c | end surface of chemical reaction device |
| 1d | side surface of chemical reaction device |
| 1e | side surface of chemical reaction device |
| 2 | first plate (process plate) |
| 2a | surface of first plate |

-continued

| | |
|---|---|
| 2b | end surface of first plate |
| 2c | end surface of first plate |
| 2d | side surface of first plate |
| 2d | side surface of first plate |
| 3 | second plate (temperature controlling plate) |
| 3a | surface of second plate |
| 3b | end surface of second plate |
| 3c | end surface of second plate |
| 3d | side surface of second plate |
| 3e | side surface of second plate |
| 4 | channel having concave trench cross-sectional shape |
| 6 | temperature controlling channel having concave trench cross-sectional shape |
| 6a | main channel having concave trench cross-sectional shape |
| 6b | feed-side channel having concave trench cross-sectional shape |
| 6c | discharge-side channel having concave trench cross-sectional shape |
| $P_0$ | prescribed interval |
| $w_0$ | width |
| $d_0$ | depth |
| L | length of channel |
| 30 | connector |
| 31 | joint part |
| 32 | connecting part |
| 40 | chemical reaction device |
| 50 | chemical reaction device |
| 60 | chemical reaction device |
| 80 | production apparatus |
| 61 | compound (A) |
| 62 | first tank |
| 63 | compound (B) |
| 64 | second tank |
| 65 | plunger pump |
| 66 | plunger pump |
| 67 | mixer |
| 68 | temperature controlling unit |
| 69 | cooling heat exchange device |
| 70 | temperature controlling unit |
| 71 | exhaust pressure valve |
| 72 | receiving vessel |
| 80 | schematic structural view showing schematically production apparatus of resin used in Examples and Comparative Examples |
| 85 | chemical reaction device |

The invention claimed is:

1. A process for continuously producing a urethane (meth)acrylate, comprising causing a mixed liquid of a compound (A) having a hydroxyl group and a (meth)acryloyl group and a compound (B) having an isocyanate group to pass continuously and densely through a tubular microchannel formed in a heat-conducting reaction device, and reacting the hydroxyl group of the compound (A) with the isocyanate group of the compound (B), the tubular microchannel in the reaction device having a space size making a fluid cross-sectional area, through which the mixed liquid passes densely, of from 0.1 to 4.0 mm$^2$, and the process comprising heating the heat-conducting reaction device to a temperature of from 100 to 250° C., reacting the mixed liquid to provide a Reynolds number of a reaction liquid passing through the tubular microchannel in a range of from 0.2 to 300, and after completing reaction, cooling continuously a reaction product discharged from the heat-conducting reaction device.

2. The production process according to claim 1, wherein the reaction product after completing reaction is cooled under a temperature condition of from 50 to 90° C.

3. The process for producing a urethane (meth)acrylate according to claim 1, wherein the compound (A) having a hydroxyl group and a (meth)acryloyl group and the compound (B) having an isocyanate group are mixed in advance to form a mixed liquid, and the mixed liquid is fed continuously to the heat-conducting reaction device.

4. The process for producing a urethane (meth)acrylate according to claim 3, wherein reaction is performed by using a reaction apparatus containing a plurality of the heat-conducting reaction devices connected in series each having the tubular microchannel formed therein.

5. The process for producing a urethane (meth)acrylate according to claim 3, wherein the heat-conducting reaction device having the tubular microchannel formed therein has a structure containing a plurality of heat-conducting plate structures each having plural trenches on a surface thereof, which are laminated on each other.

6. The process for producing a urethane (meth)acrylate according to claim 1, wherein the mixed liquid is caused to pass through the tubular microchannel at a flow velocity of from $0.9 \times 10^{-4}$ to 4.2 m/sec.

7. The process for producing a urethane (meth)acrylate according to claim 1, wherein the compound (A) is a compound having a hydroxyl value of from 50 to 500, and the compound (B) is a compound having an isocyanate percentage of from 15 to 60.

8. The process for producing a urethane (meth)acrylate according to claim 1, wherein the continuous cooling is performed by causing the reaction product to pass continuously through a cooling heat exchange device having a tubular microchannel formed therein connected to an exit of a reaction liquid of the heat-conducting reaction device.

9. The process for producing a urethane (meth)acrylate according to claim 2, wherein the compound (A) having a hydroxyl group and a (meth)acryloyl group and the compound (B) having an isocyanate group are mixed in advance to form a mixed liquid, and the mixed liquid is fed continuously to the heat-conducting reaction device.

10. The process for producing a urethane (meth)acrylate according to claim 9, wherein reaction is performed by using a reaction apparatus containing a plurality of the heat-conducting reaction devices connected in series each having the tubular microchannel formed therein.

11. The process for producing a urethane (meth)acrylate according to claim 9, wherein the heat-conducting reaction device having the tubular microchannel formed therein has a structure containing a plurality of heat-conducting plate structures each having plural trenches on a surface thereof, which are laminated on each other.

12. The process for producing a urethane (meth)acrylate according to claim 2, wherein the continuous cooling is performed by causing the reaction product to pass continuously through a cooling heat exchange device having a tubular microchannel formed therein connected to an exit of a reaction liquid of the heat-conducting reaction device.

* * * * *